(12) United States Patent
Abdat-Vindel et al.

(10) Patent No.: US 12,053,544 B2
(45) Date of Patent: Aug. 6, 2024

(54) COMPOSITION COMPRISING A NATURAL DYE, A TRIARYLMETHANE DIRECT DYE AND AN AROMATIC COMPOUND

(71) Applicant: L'OREAL, Paris (FR)

(72) Inventors: Lyna Abdat-Vindel, Saint-Ouen (FR); Agathe Lahaye, Saint-Ouen (FR); Maria Nieto, Saint-Ouen (FR); Lisa Salvemini, Clark, NJ (US)

(73) Assignee: L'OREAL, Paris (FR)

( * ) Notice: Subject to any disclaimer, the term of this patent is extended or adjusted under 35 U.S.C. 154(b) by 171 days.

(21) Appl. No.: 17/623,349

(22) PCT Filed: Jul. 3, 2020

(86) PCT No.: PCT/EP2020/068847
§ 371 (c)(1),
(2) Date: Dec. 28, 2021

(87) PCT Pub. No.: WO2021/004950
PCT Pub. Date: Jan. 14, 2021

(65) Prior Publication Data
US 2022/0362132 A1    Nov. 17, 2022

(30) Foreign Application Priority Data

Jul. 5, 2019   (FR) ...................................... 1907547

(51) Int. Cl.
*A61Q 5/10*    (2006.01)
*A61K 8/73*    (2006.01)
*A61K 8/896*   (2006.01)
*A61K 8/92*    (2006.01)

(52) U.S. Cl.
CPC ............ *A61K 8/896* (2013.01); *A61K 8/73* (2013.01); *A61K 8/92* (2013.01); *A61K 2800/432* (2013.01)

(58) Field of Classification Search
CPC . A61K 8/896; A61K 8/73; A61K 8/92; A61K 2800/432; A61K 8/922; A61K 8/9783; A61K 8/347; A61Q 5/065
USPC .......................................................... 8/405
See application file for complete search history.

(56) References Cited

U.S. PATENT DOCUMENTS

| 3,100,739 | A |  | 8/1963 | Kaiser et al. |
| 3,524,842 | A |  | 8/1970 | Grossmann et al. |
| 3,578,386 | A |  | 5/1971 | Kalopissis et al. |
| 3,617,163 | A |  | 11/1971 | Kalopissis et al. |
| 3,817,698 | A |  | 6/1974 | Kalopissis et al. |
| 3,869,454 | A |  | 3/1975 | Lang et al. |
| 3,955,918 | A |  | 5/1976 | Lang |
| 4,025,301 | A |  | 5/1977 | Lang |
| 4,886,517 | A |  | 12/1989 | Bugaut et al. |
| 5,708,151 | A |  | 1/1998 | Möckli |
| 5,750,723 | A |  | 5/1998 | Eldin et al. |
| 5,847,156 | A |  | 12/1998 | Eldin et al. |
| 5,879,413 | A |  | 3/1999 | Pengilly et al. |
| 5,919,273 | A |  | 7/1999 | Rondeau et al. |
| 5,965,148 | A |  | 10/1999 | Agostini et al. |
| 5,993,490 | A |  | 11/1999 | Rondeau et al. |
| 6,136,042 | A |  | 10/2000 | Maubru |
| 6,179,881 | B1 |  | 1/2001 | Henrion et al. |
| 6,451,069 | B2 |  | 9/2002 | Matsunaga et al. |
| 6,458,167 | B1 |  | 10/2002 | Genet et al. |
| 6,491,927 | B1 |  | 12/2002 | Arnaud et al. |
| 6,797,013 | B1 |  | 9/2004 | Lang et al. |
| 6,863,883 | B1 |  | 3/2005 | Tsujino et al. |
| 2003/0159221 | A1 | * | 8/2003 | Lang ...................... A61K 8/411 8/408 |
| 2014/0150185 | A1 | * | 6/2014 | Lalleman ............... A61Q 5/065 8/405 |
| 2019/0374452 | A1 | * | 12/2019 | Fameau ................... A61K 8/22 |

FOREIGN PATENT DOCUMENTS

| CN | 103998531 | B | * | 7/2017 | ............... A61Q 5/10 |
| CN | 107257797 | A | * | 10/2017 | ............... A61Q 5/10 |
| CN | 107501991 | A | * | 12/2017 | ............... A61Q 5/10 |
| DE | 2527638 | A1 |  | 5/1976 |  |

(Continued)

OTHER PUBLICATIONS

STIC Search Report dated Oct. 5, 2023.*
Kuznetsova et al., "The determination of Thickness of a Histological Section by Interference Microscopy," Tsitologiya, vol. 10, No. 3, (1968), pp. 403-405.
Tien, Hsien-Ju et al., "Syntheses of New Azo Dyestuff Containing a Sydnone Ring," Journal of the Chinese Chemical Society, (Taipei), (1998), 45(1), pp. 209-211.
International Search Report and Written Opinion for counterpart Application No. PCT/EP2020/068844, dated Sep. 22, 2020.
International Search Report and Written Opinion for counterpart Application No. PCT/EP2020/068847, dated Oct. 2, 2020.

(Continued)

*Primary Examiner* — Eisa B Elhilo
(74) *Attorney, Agent, or Firm* — MARBURY LAW GROUP, PLLC

(57) ABSTRACT

The present invention relates to a composition for dyeing human keratin fibers, comprising at least one natural dye, at least one triarylmethane synthetic direct dye and at least one compound of formula (I), in which Y represents a $C_1$-$C_4$ hydroxyalkyl group or a $C_1$-$C_4$ hydroxyalkyloxy radical, n denotes an integer ranging from 0 to 5, and X, which may be identical or different, represents a $C_1$-$C_4$ alkyl radical or a halogen. The invention also relates to a process for dyeing human keratin fibers using this composition.

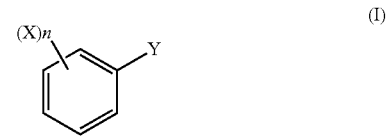

(I)

20 Claims, No Drawings

(56) References Cited

FOREIGN PATENT DOCUMENTS

| | | | | |
|---|---|---|---|---|
| DE | 2538363 | A1 | 5/1976 | |
| DE | 4137005 | A1 | 5/1993 | |
| DE | 4220388 | A1 | 12/1993 | |
| DE | 19735851 | A1 | 2/1999 | |
| EP | 0681829 | A1 * | 11/1995 | ............... A61Q 5/10 |
| EP | 0714954 | A2 | 6/1996 | |
| EP | 0850636 | A1 | 7/1998 | |
| EP | 0850637 | A1 | 7/1998 | |
| EP | 0918053 | A1 | 5/1999 | |
| EP | 1062940 | A1 | 12/2000 | |
| EP | 1133976 | A1 | 9/2001 | |
| FR | 1221122 | A | 5/1960 | |
| FR | 1516943 | A | 2/1968 | |
| FR | 1540423 | A | 9/1968 | |
| FR | 1560664 | A | 3/1969 | |
| FR | 1567219 | A | 5/1969 | |
| FR | 2189006 | A1 | 1/1974 | |
| FR | 2275462 | A1 | 1/1976 | |
| FR | 2285851 | A1 | 4/1976 | |
| FR | 2570946 | A1 | 4/1986 | |
| FR | 2757385 | A1 | 6/1998 | |
| FR | 2788433 | A1 | 7/2000 | |
| FR | 2907672 | A1 * | 5/2008 | ............... A61Q 5/10 |
| FR | 3045331 | A1 * | 6/2017 | ............. A61Q 5/065 |
| FR | 3059547 | A1 * | 6/2018 | ............... A61K 8/41 |
| FR | 3075637 | A1 | 6/2019 | |
| GB | 738585 | A | 10/1955 | |
| GB | 1163385 | A | 9/1969 | |
| GB | 1195386 | A | 6/1970 | |
| GB | 1514466 | A | 6/1978 | |
| WO | 95/01772 | A1 | 1/1995 | |
| WO | 95/15144 | A1 | 6/1995 | |
| WO | 97/44004 | A1 | 11/1997 | |
| WO | 99/48465 | A1 | 9/1999 | |
| WO | 01/66646 | A1 | 9/2001 | |
| WO | 2013/083699 | A1 | 6/2013 | |
| WO | WO 20180096132 | A1 * | 5/2018 | ............... A61Q 5/10 |
| WO | WO 2018115393 | A1 * | 6/2018 | ............... A61Q 5/10 |
| WO | 2021/004948 | A1 | 1/2021 | |

OTHER PUBLICATIONS

Seidler et al., "The qualification of different ditetrazolium salts as indicators in the oxido-reductase histochemistry," Acta histochem, Bc. 61 (1), (1978), pp. 48-52.

Alberti et al., "Ricerche Sui Coloranti Cationici Per Fibra Acrilica," La Chimica E L'Industria, vol. 56, No. 9, Sep. 1974, pp. 600-602.

Savarino et al., "Disperse and Cationic Dyes from Aminophenyl-X-Azolo-Pyridines," Dyes and Pigments 11 (1989), pp. 163-172.

Viscardi, Guido et al., "Disperse Cationic Azo Dyes from Heterocyclic Intermidiates," Dyes and Pigments, vol. 19, No. 1, (1992), pp. 69-79.

Neidlein, Richard et al., "Synthese von Substituierten Pyridiniumsalzen," German Monatshefte für Chemie, (1975), vol. 106, No. 3, pp. 643-648 (English translation unavailable).

Zhousheng et al., "Research and Application of the Coordination Reaction of New Fluorescent Reagent CCPAR and CU(II)," Huazue Fence, vol. 29, No. 4, (1993), pp. 233-234.

Mintel: "Colour Safe Hair Mask," Ishizawa Laboratories, XP055661276, Record No. 3171553, May 1, 2015.

Mintel: "Hair Color Treatment," Avon, XP055660882, Record No. 4399863, Aug. 15, 2016.

Mintel, "Mangala Fashion Toner Treatment," Hans Conzen Kosmetik, XP05566169, Record No. 5609217, Aug. 9, 2018.

Mintel: "Temporary Color Gel," Colorist Christophe, XP055661262, Record No. 5996259, Sep. 18, 2018.

Balaban et al., "Reactions of Pyrylium Salts with Nucleophiles, XX. Synthesis of 4-(N-Pyridinium)-4'-Dialkylamino Azobenzene and of 4-(4-Dialkylaminophenylazo)-4'-(N-Pyridinium)-Biphenyl Derivatives," Revue Roumaine de Chimie, 33, (1988), pp. 377-383.

Alberti et al., "Thermodynamic Features in Acrylic Fiber Dyeing with Basic Dyes," Textile Research Institute, 54(2), Feb. 1984, pp. 105-107.

Stashkevich et al., "Bisformazans and bistetrazolium salts, derivatives of quinaldine quaternary salts," Zhurnal Obshchei Khimii (1970), 40(1), pp. 195-202 (partial GB translation).

Yen, et al., "The Design and Synthesis of Bisazo Series Compound Used in Organophotoconductor," MRL Bull. Res. Dev., vol. 6, No. 2 (1992), pp. 21-27).

\* cited by examiner

COMPOSITION COMPRISING A NATURAL DYE, A TRIARYLMETHANE DIRECT DYE AND AN AROMATIC COMPOUND

CROSS REFERENCE TO RELATED APPLICATION

This is a national stage application of PCT/EP2020/068847, filed internationally on Jul. 3, 2020, which claims priority to French Application No. 1907547, filed on Jul. 5, 2019, both of which are incorporated by reference herein in their entireties.

The present invention relates to a composition for dyeing human keratin fibers, notably the hair, comprising at least one natural dye, at least one triarylmethane synthetic direct dye and at least one particular aromatic compound. The invention also relates to a dyeing process using this composition.

Two major methods for dyeing human keratin fibers, and in particular the hair, are known.

One of these two methods is oxidation dyeing or permanent dyeing. This dyeing method uses one or more oxidation dye precursors, usually one or more oxidation bases optionally combined with one or more couplers.

In general, oxidation bases are chosen from ortho- or para-phenylenediamines, ortho- or para-aminophenols and heterocyclic compounds. These oxidation bases are colorless or weakly colored compounds which, when combined with oxidizing products, can give access to colored species.

The shades obtained with these oxidation bases are quite often varied by combining them with one or more couplers, these couplers being notably chosen from aromatic meta-diamines, meta-aminophenols, meta-diphenols and certain heterocyclic compounds such as indole compounds.

The variety of molecules used as oxidation bases and couplers allows a wide range of colors to be obtained. This type of dyeing also makes it possible to obtain permanent colorings, but the use of oxidizing agents may lead to degradation of the keratin fibers.

The second dyeing method, known as direct dyeing or semi-permanent dyeing, comprises the application of direct dyes, which are molecules with affinity for the fibers and which color even in the absence of an oxidizing agent added to the compositions containing them. Given the nature of the molecules used, they tend rather to remain on the surface of the fiber and penetrate relatively little into the fiber, when compared with the small molecules of oxidation dye precursors.

The direct dyes generally used are chosen from nitrobenzene, anthraquinone, nitropyridine, azo, methine, azomethine, xanthene, acridine, azine and triarylmethane direct dyes. The chemical species used may be nonionic, anionic (acidic dyes) or cationic (basic dyes). Direct dyes may also be natural dyes.

Dyeing the hair using natural direct dyes has been known since ancient times.

Compositions containing one or more natural direct dyes are applied to the keratin fibers for a time necessary to obtain the desired coloring, and are then rinsed out.

However, the colorings resulting therefrom are colorings that may be particularly chromatic, but which are, however, only temporary or semi-permanent since their desorption from the surface and/or the core of the fiber is responsible for their weak dyeing power and their poor persistence with respect to washing. Moreover, these compositions require relatively long leave-on times. They may vary from several tens of minutes to several hours (overnight) depending on the desired intensity, with no ability to control the result. The result varies as a function of the fibers to be dyed and of the nature of the natural dye(s) used.

One of the aims of the present invention is to propose colorings which are based on natural dyes and which offer a wide range of resistant shades, are respectful of the hair's nature and have a reduced leave-on time, notably so as to overcome stability problems of the composition and to optimize the working qualities, while at the same time retaining powerful, chromatic and homogeneous colorings, between the end and the root of the same fiber and from one fiber to another.

This aim is achieved by the present invention, one subject of which is a composition for dyeing human keratin fibers, notably the hair, comprising at least one natural dye, at least one triarylmethane synthetic direct dye and at least one aromatic compound of formula (I), in which Y represents a $C_1$-$C_4$ hydroxyalkyl group or a $C_1$-$C_4$ hydroxyalkyloxy radical, n denotes an integer ranging from 0 to 5, and X, which may be identical or different, represents a $C_1$-$C_4$ alkyl radical or a halogen.

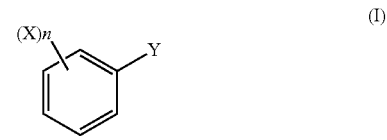

(I)

The invention also relates to a process for dyeing human keratin fibers, which consists in applying the composition of the invention to the fibers.

The invention can thus induce very satisfactory "buildup" and/or power of the color, with a wide range of shades in reduced leave-on times.

Other subjects, features, aspects and advantages of the present invention will emerge even more clearly on reading the description and the examples that follow.

In the description, the term "at least one" is equivalent to "one or more".

For the purposes of the present invention, the term "buildup" of the color on keratin fibers means the variation in coloring between locks of undyed hair and locks of dyed hair.

Natural Dye(s)

The composition according to the invention comprises at least one natural dye.

In the context of the invention, the term "natural dye" means any dye or dye precursor from a natural source, in particular of plant origin. The natural dyes may notably be obtained by extraction (and optionally purification) from a plant matrix, by grinding plants or plant parts, roots, wood, bark, berries, lichens, leaves, flowers, nuts or seeds. Natural dyes may also be obtained by fermentation.

The natural dye(s) are chosen, for example, from lawsone, juglone, alizarin, purpurin, carminic acid, kermesic acid, laccaic acid, purpurogallin, anthragallol protocatechaldehyde, indigo, isatin, curcumin, spinulosin, chlorophylls, chlorophyllines, orceins, hematin, hematoxylin, brazilin, brazileine, santaline, santarubin, carthamine, flavonoids (with, for example, morin, apigenidin and quercetin), anthocyans (such as apigeninidin), carotenoids and anthraquinones, or mixtures thereof.

Extracts, decoctions or ground matter, notably powders, containing these natural dyes and notably extracts, decoctions or ground matter obtained, for example, from pernambuco wood, campeachy wood, sandalwood, orchil, turmeric, madder, indigo-producing plants such as indigo plant, sorghum, carrot, annatto, Brazil wood, safflower, henna, plants of the *Cassia* family, in particular *Cassia angustifolia* (*senna*), or *Cassia auriculata* or *Cassia italica*, or mixtures thereof, may also be used.

In particular, the composition according to the invention may comprise indigo-producing plant powder and/or extract. (For the purposes of the present invention, the term "indigo-producing plant extract" means "a dye extract from an indigo-producing plant").

As indigo-producing plants, mention may be made of numerous species derived from the following genera:

*Indigofera* such as *Indigofera tinctoria Indigo suffruticosa, Indigofera articulata, Indigofera arrecta, Indigofera gerardiana, Indigofera argentea, Indigofera Indigofera longiracemosa;*
*Isatis* such as *Isatis tinctoria;*
*Polygonum* or *Persicaria* such as *Polygonum tinctorium* (*Persicaria tinctoria*);
*Wrightia* such as *Wrightia tinctoria;*
*Calanthe* such as *Calanthe veratrifolia;* and
*Baphicacanthus* such as *Baphicacanthus cusia.*

Preferably, the indigo-producing plant is of the genus *Indigofera* and more particularly is *Indigofera tinctoria, suffruticosa* or *argentea*, preferably *Indigofera tinctoria.*

Use may be made of all or part (in particular the leaves notably for *Indigofera tinctoria*) of the indigo-producing plant.

The composition according to the invention may contain henna.

According to the present invention, the term "henna" refers to a henna plant powder and/or a henna plant dye extract, preferably from a henna plant such as *Lawsonia alba* or *Lawsonia inermis*. The henna plant powder and/or dye extract notably comprises lawsone and/or a glucosyl precursor thereof.

Preferably, the henna used according to the present invention is in powder form.

The henna used in the invention is preferably red henna (*Lawsonia inermis*, alba). Lawsone [83-72-7] (CI Natural Orange 6; CI 75420), also known as isojuglone, may be found in henna shrubs (*Lawsonia alba, Lawsonia inermis*). Preferably, the henna is in powder form.

The composition according to the invention may comprise a powder or a plant extract of the *Cassia* family, in particular *Cassia angustifolia* and/or *Cassia auriculata* and/or *Cassia italica*, preferably *Cassia angustifolia.*

When the natural dye(s) are in powder form, the powder may be screened to obtain particles with upper limit sizes corresponding to the orifices or mesh sizes of the screen, particularly between 35 and 80 mesh (US). According to a particular embodiment of the invention, the size of the powder particles is fine. According to the invention, a particle size of less than or equal to 500 µm is more particularly intended. Preferentially, the powder is constituted of fine particles with sizes inclusively between 10 and 300 µm and more particularly between 50 and 250 µm. It is understood that said particles preferentially have a moisture content of between 0 and 10% by weight, relative to the total weight of the powders.

Preferably, the natural dye(s) are chosen from lawsone, henna extracts and/or powders, indigo, indigo-producing plant extracts and/or powders, plant extracts and/or powders of the *Cassia* family, in particular *Cassia angustifolia*, and/or *Cassia auriculata* and/or *Cassia italica*, and/or mixtures thereof.

More preferentially, the natural dye(s) are chosen from lawsone, henna extracts and/or powders, *Cassia angustifolia* extracts and/or powders, indigo, indigo-producing plant extracts and/or powders, and/or mixtures thereof.

Even more preferentially, the natural dye(s) are chosen from lawsone, henna extracts and/or powders, *Cassia angustifolia* extracts and/or powders, and/or mixtures thereof.

According to a particular embodiment, the total amount of natural dyes ranges from 40% to 98% by weight, preferably from 50% to 95% by weight and better still from 60% to 90% by weight, relative to the total weight of the composition.

Triarylmethane Synthetic Direct Dye(s)

The composition according to the invention comprises at least one triarylmethane synthetic direct dye.

The term "synthetic direct dye" means any dye which is different from an oxidation dye, that is not naturally present and is only obtained via chemical synthesis. In particular, it is a dye which is not obtained from a plant matrix or by fermentation and which diffuses superficially on the fiber.

In particular, the triarylmethane dye(s) of the invention may be cationic, anionic, neutral or zwitterionic.

Preferably, the dye(s) of the invention are chosen from the triarylmethane dyes of formula (IIa) or (IIb), and also the addition salts thereof with an organic or mineral acid or base, the geometrical isomers, optical isomers or tautomers thereof, and the mesomeric forms thereof, the solvates thereof such as hydrates, in which A, B and C are identical or different and represent an optionally substituted (hetero) aryl group such as phenyl.

(IIa)

(IIb)

According to one embodiment, the direct dyes of formula (II) are cationic.

The term "cationic direct dye" refers commonly to dyes known as "basic" direct dyes or "basic dyes" on account of their affinity for acidic substances, notably including in their structure at least one endocyclic or exocyclic cationic or cationizable group. In particular, the charge may be borne by an aryl or heteroaryl group.

Preferably, the triarylmethane direct dye(s) according to the invention are cationic dyes of formulae (IIa$_1$) and (IIa$_2$) below, and also the addition salts thereof with an organic or mineral acid or base, the geometrical isomers, optical isomers or tautomers thereof, the mesomeric forms thereof, and the solvates thereof such as hydrates:

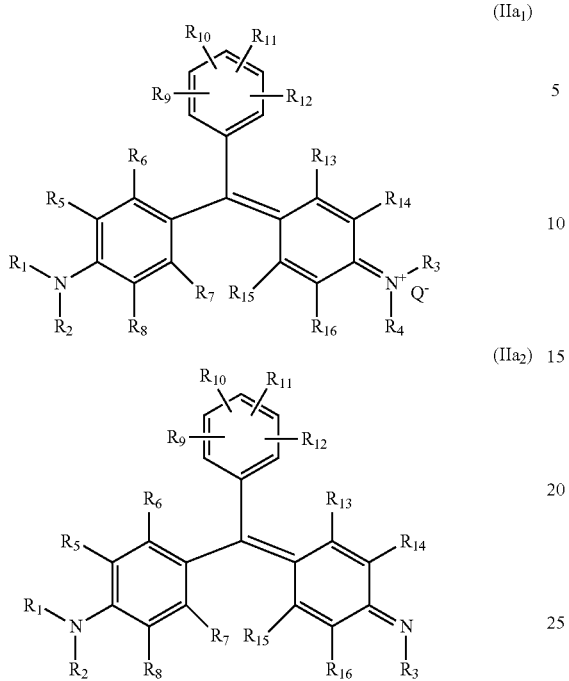

in which:

R1, R2, R3 and R4, which may be identical or different, represent a hydrogen atom or a group from among: $(C_1-C_6)$alkyl which is optionally substituted, preferably with a hydroxyl group; aryl such as phenyl, aryl$(C_1-C_4)$alkyl such as benzyl, heteroaryl, heteroaryl$(C_1-C_4)$alkyl, or alternatively two groups R1 and R2, and/or R3 and R4, borne by the same nitrogen atom form, together with the nitrogen atom which bears them, an optionally substituted heterocycloalkyl group such as morpholino, piperazino or piperidino; preferably, R1, R2, R3 and R4, which may be identical or different, represent a hydrogen atom or a $(C_1-C_4)$alkyl group;

R5, R6, R7, R8, R9, R10, R11, R12, R13, R14, R15 and R16, which may be identical or different, represent a hydrogen or halogen atom, or a group chosen from i) hydroxyl, ii) thiol, iii) amino, iv) (di)$(C_1-C_4)$(alkyl)amino, v) (di)arylamino such as (di)phenylamino, vi) nitro, vii) acylamino (—NR—C(O)R') in which the radical R is a hydrogen atom, a $C_1-C_4$ alkyl radical optionally bearing at least one hydroxyl group and the radical R' is a $C_1-C_2$ alkyl radical; viii) carbamoyl ((R)$_2$N—C(O)—) in which the radicals R, which may be identical or not, represent a hydrogen atom, a $C_1-C_4$ alkyl radical optionally bearing at least one hydroxyl group; ix) carboxylic acid or ester, (—O—C(O)R') or (—C(O)OR'), in which the radical R' is a hydrogen atom, or $C_1-C_4$ alkyl optionally bearing at least one hydroxyl group and the radical R' is a $C_1-C_2$ alkyl radical; x) alkyl which is optionally substituted, notably with a hydroxyl group; xi) alkylsulfonylamino (R'SO$_2$—NR—) in which the radical R represents a hydrogen atom, a $C_1-C_4$ alkyl radical optionally bearing at least one hydroxyl group and the radical R' represents a $C_1-C_4$ alkyl radical, a phenyl radical; xii) aminosulfonyl ((R)$_2$N—SO$_2$—) in which the radicals R, which may be identical or not, represent a hydrogen atom or a $C_1-C_4$ alkyl radical optionally bearing at least one hydroxyl group, xiii) $(C_1-C_4)$alkoxy, and xiv) $(C_1-C_4)$alkylthio;

or alternatively two radicals borne by two contiguous carbon atoms R5 and R6 and/or R7 and R8, and/or R9 and R10 and/or R11 and R12 and/or R13 and R14 and/or R15 and R16 form, together with the carbon atoms which bear them, a fused 6-membered aryl or heteroaryl ring, preferably benzo, said ring also possibly being optionally substituted, preferably an unsubstituted benzo ring;

Q$^-$ represents an anionic counterion to achieve electrical neutrality, preferably chosen from halides such as chloride or bromide, and phosphate.

When the cationic dye comprises one or more anionic substituents such as COOR or SO$_3$R with R denoting a hydrogen or a cation, it is understood that there are then more cationic substituents than anionic substituents, such that the overall resulting charge of the triarylmethane structure is cationic.

According to a preferred embodiment, the triarylmethane dye(s) of the invention are chosen from those of formula (IIa$_1$) or (IIa$_2$), in which, taken together or separately, R1, R2, R3 and R4 represent a hydrogen atom or a $(C_1-C_4)$alkyl group such as methyl or ethyl, R5, R6, R7, R8, R9, R10, R11, R12, R13, R14, R15 and R16 represent a hydrogen atom, a halogen atom, such as chlorine, or a $(C_1-C_4)$alkyl group such as methyl or ethyl, an amino group, a (di)$(C_1-C_4)$(alkyl)amino group and, preferably, at least one of the groups R9, R10, R11 or R12 represents a hydrogen atom, a halogen atom (Cl), or an amino group, or a $(C_1-C_4)$(alkyl)amino or (di)$(C_1-C_4)$(alkyl)amino group, preferably in the para position relative to the phenyl group.

The term "anionic counterion" means an anion or an anionic group derived from an organic or mineral acid salt which counterbalances the cationic charge of the dye; more particularly, the anionic counterion is chosen from: i) halides such as chloride or bromide; ii) nitrates; iii) sulfonates, including $C_1-C_6$ alkylsulfonates: Alk-S(O)2O— such as methanesulfonate or mesylate, and ethanesulfonate; iv) arylsulfonates: Ar—S(O)2O— such as benzenesulfonate and toluenesulfonate or tosylate; v) citrate; vi) succinate; vii) tartrate; viii) lactate; ix) alkyl sulfates: Alk-O—S(O)O— such as methyl sulfate and ethyl sulfate; x) aryl sulfates: Ar—O—S(O)O— such as benzene sulfate and toluene sulfate; xi) alkoxy sulfates: Alk-O—S(O)2O— such as methoxy sulfate and ethoxy sulfate; xii) aryloxy sulfates: Ar—O—S(O)2O—, xiii) phosphates O=P(OH)2-O—, O=P(O-)2-OH O=P(O-)3, HO—[P(O)(O—)]w-P(O)(O-)2 with w being an integer; xiv) acetate; xv) triflate; and xvi) borates such as tetrafluoroborate, xvii) disulfate (O=)2S(O-)2 or SO$_4^{2-}$ and monosulfate HSO$_4^-$.

The term "cationic counterion" means alkali metal or alkaline-earth metal cations, or organic cations such as ammoniums; preferably, the anionic counterions of the invention are chosen from alkali metals such as Na$^+$ or K$^+$.

A "cationic heteroaryl radical" is a heteroaryl group as defined previously, which includes a quaternized endocyclic or exocyclic cationic group.

When the cationic charge is endocyclic, it is included in the electron delocalization via the mesomeric effect; for example, it is a pyridinium, imidazolium or indolinium group:

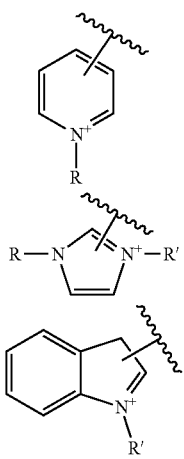

with R and R' being a heteroaryl substituent as defined previously and particularly a (hydroxy)($C_1$-$C_8$)alkyl group such as methyl.

When the charge is exocyclic, for example, it is an ammonium or phosphonium substituent $R^+$ such as trimethylammonium, which is exterior to the heteroaryl such as pyridyl, indolyl, imidazolyl or naphthalimidyl in question:

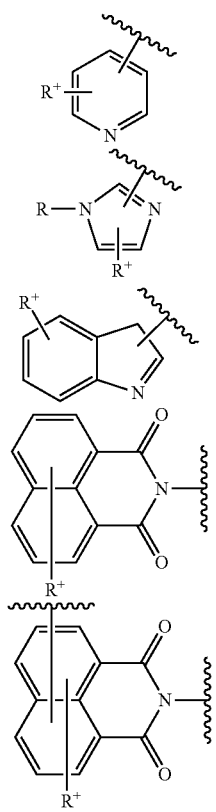

with R being a heteroaryl substituent as defined previously and R+ an ammonium RaRbRcN$^+$—, phosphonium RaRbRcP$^+$— or ammonium RaRbRcN$^+$—($C_1$-$C_6$)alkylamino with Ra, Rb and Rc, which may be identical or different, representing a hydrogen atom or a ($C_1$-$C_8$)alkyl group such as methyl.

The term "cationic aryl bearing an exocyclic charge" means an aryl ring whose quaternized cationic group is outside the said ring: it is notably an ammonium or phosphonium substituent $R^+$ such as trimethylammonium, which is outside the aryl such as phenyl or naphthyl:

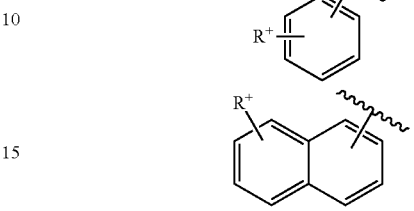

Preferably, the triarylmethane direct dye(s) are chosen from Basic Violet 1, Basic Violet 2, Basic Violet 3, Basic Violet 4, Basic Violet 14, Basic Blue 1, Basic Blue 7, Basic Blue 26, Basic Green 1, Basic Blue 77 (also known as HC Blue 15), or mixtures thereof, better still from Basic Violet 2, HC Blue 15, or mixtures thereof.

According to a particular embodiment, the total amount of triarylmethane synthetic direct dye(s) ranges from 0.01% and 20% by weight, preferably between 0.05% and 15% by weight, better still between 0.1% and 13% by weight relative to the total weight of the composition.

Aromatic Compound of Formula (I)

The composition according to the invention comprises at least one compound of formula (I) in which Y represents a $C_1$-$C_4$ hydroxyalkyl group or a $C_1$-$C_4$ hydroxyalkyloxy radical, n denotes an integer ranging from 0 to 5, and X, which may be identical or different, represents a $C_1$-$C_4$alkyl radical or a halogen.

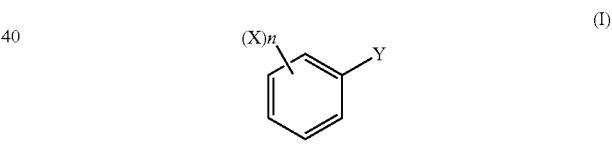

Preferably, n is equal to 0. According to a particular embodiment, Y represents a hydroxymethyl, hydroxyethyl or hydroxyethyloxy radical.

As examples of compounds of formula (I), mention may be made of benzyl alcohol, phenylethanol and phenoxyethanol.

According to a particular embodiment, the compound of formula (I) is benzyl alcohol.

According to a particular embodiment, the total amount of aromatic compounds of formula (I) ranges between 0.1% and 20% by weight relative to the total weight of the composition, preferably from 0.5% to 15% by weight and preferentially from 1% to 10% by weight relative to the total weight of the composition.

According to one embodiment, the dye composition according to the invention comprises:
- at least one natural dye chosen from lawsone, henna extracts and/or powders, *Cassia angustifolia* extracts and/or powders, indigo, indigo-producing plant extracts and/or powders, or mixtures thereof;
- at least one triarylmethane synthetic direct dye of formula (IIa$_1$) or (IIa$_2$);

at least one aromatic compound of formula (I) chosen from benzyl alcohol, phenylethanol and phenoxyethanol, preferably benzyl alcohol.

According to a particular embodiment, the composition according to the invention comprises:
- at least one natural dye chosen from lawsone, henna extracts and/or powders, *Cassia angustifolia* extracts and/or powders, indigo, indigo-producing plant extracts and/or powders, or mixtures thereof;
- at least one triarylmethane synthetic direct dye chosen from Basic Violet 1, Basic Violet 2, Basic Violet 3, Basic Violet 4, Basic Violet 14, Basic Blue 1, Basic Blue 7, Basic Blue 26, Basic Green 1, or mixtures thereof, better still from Basic Violet 2, HC Blue 15, or mixtures thereof;
- at least one compound of formula (I), chosen from benzyl alcohol, phenylethanol and phenoxyethanol, or mixtures thereof, preferably benzyl alcohol.

According to this particular embodiment, the total amount of natural dye(s) chosen from lawsone, henna extracts and/or powders, *Cassia angustifolia* extracts and/or powders, indigo, indigo-producing plant extracts and/or powders, or mixtures thereof, preferably ranges from 60% to 90% by weight, relative to the total weight of the composition; the amount of triarylmethane synthetic direct dye(s) chosen from the dyes of formula (IIa$_1$) or (IIa$_2$), or mixtures thereof, ranges from 0.1% to 13% by weight relative to the total weight of the composition; the amount of compound(s) of formula (I) chosen from benzyl alcohol, phenylethanol and phenoxyethanol, or mixtures thereof, ranges from 1% to 10% by weight relative to the total weight of the composition.

According to a preferred embodiment, the composition according to the invention comprises:
- at least one natural dye chosen from lawsone, henna extracts and/or powders, *Cassia angustifolia* extracts and/or powders, indigo, indigo-producing plant extracts and/or powders, or mixtures thereof;
- at least one triarylmethane synthetic direct dye chosen from Basic Violet 2, HC Blue 15, or mixtures thereof;
- at least benzyl alcohol.

According to this preferred embodiment, the total amount of lawsone, of henna extracts and/or powders, of *Cassia angustifolia* extracts and/or powders, of indigo, of indigo-producing plant extracts and/or powders, or of mixtures thereof, preferably ranges from 60% to 90% by weight, relative to the total weight of the composition; the total amount of Basic Violet 2, of HC Blue 15, or of mixtures thereof ranges from 0.1% and 13% by weight relative to the total weight of the composition; the amount of benzyl alcohol ranges between 1% and 10% by weight relative to the total weight of the composition.

Additional Synthetic Direct Dyes

According to one embodiment, the composition according to the invention may comprise one or more synthetic direct dyes which are different from the triarylmethane dyes described previously.

These direct dyes are, for example, chosen from the dyes conventionally used for direct dyeing, and among which mention may be made of all the aromatic and/or nonaromatic dyes commonly used, such as azo direct dyes, hydrazono direct dyes, nitro(hetero)aryl direct dyes, (poly)methine direct dyes such as cyanines or hemicyanines, styryl direct dyes, carbonyl direct dyes, azine direct dyes, porphyrin direct dyes, metalloporphyrin direct dyes, quinone direct dyes and in particular anthraquinone direct dyes, indoamine direct dyes, phthalocyanine direct dyes, and fluorescent dyes.

By way of example, mention may be made of the dyes Basic Red 51, Basic Orange 31 and Basic Yellow 87 or derivatives thereof:

Basic Red 51

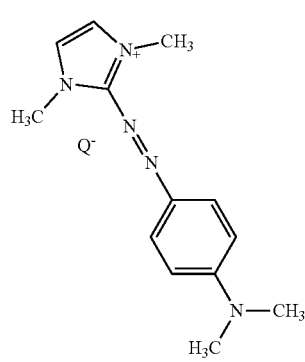

Basic Orange 31

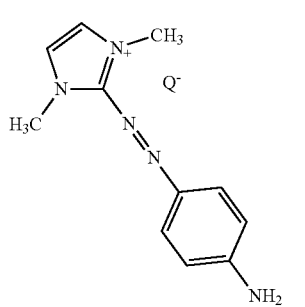

Basic Yellow 87

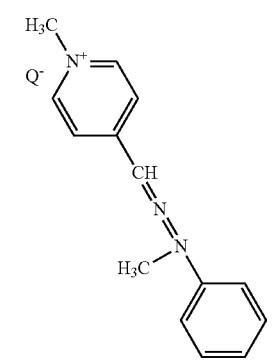

with Q⁻ an anionic counterion as defined previously, in particular a halide, such as chloride, or an alkyl sulfate, such as methyl sulfate or mesityl.

Among the nitroaryl dyes that may be mentioned are: HC Blue 2, HC Yellow 2, HC Red 3,4-hydroxypropylamino-3-nitrophenol, N,N'-bis(2-hydroxyethyl)-2-nitro-phenylenediamine. Preferably, the nitroaryl dye that is useful according to the invention is HC Blue 2.

Among the quinone direct dyes that may be mentioned are: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diaminoanthraquinone, 2-aminoethylaminoanthraquinone, 1,4-bis(β,γ-dihydroxypropylamino)anthraquinone, Acid Blue 25, Acid Blue 43, Acid Blue 78, Acid Blue 129, Acid Blue 138, Acid Blue 140, Acid Blue 251, Acid Green 25, Acid Green 41, Acid Violet 42, Mordant Red 3, Acid Black 48, HC Blue 16.

Among the azine dyes that may be mentioned are: Basic Blue 17, Basic Red 2.

Among the indoamine dyes that may be mentioned are: 2-β-hydroxyethlyamino-5-[bis(β-4'-hydroxyethyl)amino] anilino-1,4-benzoquinone, 2-β-hydroxyethylamino-5-(2'-methoxy-4'-amino)anilino-1,4-benzoquinone, 3-N-(2'-chloro-4'-hydroxy)phenylacetylamino-6-methoxy-1,4-benzoquinoneimine, 3-N-(3'-chloro-4'-methylamino)phenylureido-6-methyl-1,4-benzoquinoneimine, 3-[4'-N-(ethylcarbamylmethyl)amino]phenylureido-6-methyl-1,4-benzoquinoneimine.

According to a particular embodiment of the invention, the additional synthetic direct dye(s) are chosen from hydrazono, azo, nitro(hetero)aryl and anthraquinone dyes, or mixtures thereof.

According to a preferred embodiment of the invention, the additional synthetic direct dye(s) are chosen from Basic Yellow 87, Basic Red 51, Basic Orange 31, HC Blue 2 and HC Blue 16, or mixtures thereof.

According to a particular embodiment, the total amount of additional synthetic direct dye(s) ranges from 0.01% to 15% by weight, preferably 0.05% to 13% by weight, relative to the total weight of the composition.

According to one embodiment, the dye composition according to the invention comprises:
- at least one natural dye chosen from lawsone, henna extracts and/or powders, *Cassia angustifolia* extracts and/or powders, indigo, indigo-producing plant extracts and/or powders, or mixtures thereof;
- at least one triarylmethane synthetic direct dye of formula $(IIa_1)$ or $(IIa_2)$;
- at least one aromatic compound of formula (I) chosen from benzyl alcohol, phenylethanol and phenoxyethanol, preferably benzyl alcohol;
- at least one additional synthetic direct dye different from the triarylmethane synthetic direct dyes.

According to a particular embodiment, the composition according to the invention comprises:
- at least one natural dye chosen from lawsone, henna extracts and/or powders, *Cassia angustifolia* extracts and/or powders, indigo, indigo-producing plant extracts and/or powders, or mixtures thereof;
- at least triarylmethane synthetic direct dye chosen from Basic Violet 1, Basic Violet 2, Basic Violet 3, Basic Violet 4, Basic Violet 14, Basic Blue 1, Basic Blue 7, Basic Blue 26, Basic Green 1, or mixtures thereof, better still from Basic Violet 2, HC Blue 15, or mixtures thereof;
- at least one compound of formula (I), chosen from benzyl alcohol, phenylethanol and phenoxyethanol, or mixtures thereof, preferably benzyl alcohol;
- at least one additional synthetic direct dye chosen from hydrazono, azo, nitro(hetero)aryl and anthraquinone dyes, or mixtures thereof.

According to this particular embodiment, the total amount of natural dye(s) chosen from lawsone, henna extracts and/or powders, *Cassia angustifolia* extracts and/or powders, indigo, indigo-producing plant extracts and/or powders, or mixtures thereof, preferably ranges from 60% to 90% by weight, relative to the total weight of the composition; the amount of triarylmethane synthetic direct dye(s) chosen from the dyes of formula $(IIa_1)$ or $(IIa_2)$, or mixtures thereof, ranges from 0.1% to 13% by weight relative to the total weight of the composition; the amount of compound(s) of formula (I) chosen from benzyl alcohol, phenylethanol and phenoxyethanol, or mixtures thereof, ranges from 1% to 10% by weight relative to the total weight of the composition; the amount of additional synthetic direct dye(s) chosen from hydrazono, azo, nitro(hetero)aryl and anthraquinone dyes, or mixtures thereof, ranges from 0.05% to 13% by weight relative to the total weight of the composition.

According to a preferred embodiment, the composition according to the invention comprises:
- at least one natural dye chosen from lawsone, henna extracts and/or powders, *Cassia angustifolia* extracts and/or powders, indigo, indigo-producing plant extracts and/or powders, or mixtures thereof;
- at least one triarylmethane synthetic direct dye chosen from Basic Violet 2, HC Blue 15, or mixtures thereof;
- at least benzyl alcohol;
- at least one additional synthetic direct dye chosen from Basic Yellow 87, Basic Red 51, Basic Orange 31, HC Blue 2 and HC Blue 16, or mixtures thereof.

According to this preferred embodiment, the total amount of lawsone, henna extracts and/or powders, extracts and/or powders of *Cassia angustifolia*, indigo, indigo-producing plant extracts and/or powders, or mixtures thereof, preferably ranges from 60% to 90% by weight, relative to the total weight of the composition; the total amount of Basic Violet 2, HC Blue 15, or of mixtures thereof, ranges from 0.1% to 13% by weight relative to the total weight of the composition; the amount of benzyl alcohol ranges between 1% to 10% by weight relative to the total weight of the composition, the total amount of Basic Yellow 87, Basic Red 51, Basic Orange 31, HC Blue 2, HC Blue 16, or mixtures thereof, ranges from 0.05% to 13% by weight relative to the total weight of the composition.

Oil(s)

The composition according to the invention may comprise one or more oils.

For the purposes of the invention, the term "oil" means a "fatty substance" that is liquid at a temperature of 30° C. and at atmospheric pressure (760 mmHg). The viscosity at 25° C. is preferably less than 1200 cps and better still less than 500 cps (defined, for example, from the Newtonian plateau determined using an ARG2 rheometer from TA Instruments equipped with a spindle with cone-plate geometry 60 mm in diameter and with an angle of 2 degrees over a shear stress range of from 0.1 Pa to 100 Pa).

The term "fatty substance" means an organic compound that is insoluble in water at ordinary temperature (25° C.) and at atmospheric pressure (760 mmHg) (solubility of less than 5% by weight, preferably less than 1% by weight and even more preferentially less than 0.1% by weight). They generally have in their structure at least one hydrocarbon-based chain including at least 6 carbon atoms. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The term "nonsilicone oil or fatty substance" refers to an oil or a fatty substance not containing any Si—O bonds and the term "silicone oil or fatty substance" refers to an oil or a fatty substance containing at least one Si—O bond.

More particularly, the oils that are useful according to the invention are chosen from nonsilicone oils and in particular $C_6$-$C_{16}$ hydrocarbons or hydrocarbons containing more than 16 carbon atoms and in particular alkanes; triglyceride oils of plant origin; essential oils; glycerides of synthetic origin, fatty alcohols; fatty acid and/or fatty alcohol esters other than triglycerides.

Preferably, the oils that are useful according to the invention are not (poly)oxyalkylenated or (poly)glycerolated ethers.

Preferably, the oils that are useful according to the invention are not fatty acids in salified form giving water-soluble soaps.

It is recalled that, for the purposes of the invention, fatty alcohols, esters and acids more particularly bear at least one linear or branched, saturated or unsaturated hydrocarbon-based group comprising 6 to 30 carbon atoms, which is optionally substituted, in particular with one or more hydroxyl groups (in particular 1 to 4). If they are unsaturated, these compounds may comprise one to three conjugated or unconjugated carbon-carbon double bonds.

As regards the $C_6$-$C_{16}$ liquid hydrocarbons, they are linear, branched or optionally cyclic, and are preferably alkanes. Examples that may be mentioned include hexane, cyclohexane, undecane, dodecane, isododecane, tridecane or isoparaffins, such as isohexadecane or isodecane, or mixtures thereof. The linear or branched hydrocarbons of mineral or synthetic origin comprising more than 16 carbon atoms are preferably chosen from liquid paraffins, liquid petroleum jelly, polydecenes and hydrogenated polyisobutene such as Parleam®, or mixtures thereof.

Among the triglycerides of plant or synthetic origin, mention may be made of liquid fatty acid triglycerides including from 6 to 30 carbon atoms, for instance heptanoic or octanoic acid triglycerides, or alternatively, for example, sunflower oil, corn oil, soybean oil, marrow oil, grapeseed oil, sesame oil, hazelnut oil, apricot oil, macadamia oil, arara oil, sunflower oil, castor oil, avocado oil, coconut oil, caprylic/capric acid triglycerides, for instance those sold by the company Stéarinerie Dubois or those sold under the names Miglyol® 810, 812 and 818 by the company Dynamit Nobel, jojoba oil and shea butter oil.

The liquid fatty alcohols that are suitable for use in the invention are more particularly chosen from linear or branched, saturated or unsaturated alcohols including from 6 to 30 carbon atoms and preferably from 8 to 30 carbon atoms. Examples that may be mentioned include octyldodecanol, 2-butyloctanol, 2-hexyldecanol, 2-undecylpentadecanol, isostearyl alcohol, oleyl alcohol, linolenyl alcohol, ricinoleyl alcohol, undecylenyl alcohol and linoleyl alcohol, or mixtures thereof.

As regards the liquid esters of fatty acids and/or of fatty alcohols other than the triglycerides mentioned above, mention may be made notably of esters of saturated or unsaturated, linear $C_3$-$C_{29}$ or branched $C_4$-$C_{30}$ aliphatic monoacids or polyacids and of saturated or unsaturated, linear $C_3$-$C_{29}$ or branched $C_4$-$C_{30}$ aliphatic monoalcohols or polyalcohols, the total carbon number of the esters being greater than or equal to 6 and more advantageously greater than or equal to 10. Esters of a fatty acid and/or of a fatty alcohol, for instance Purcellin oil (stearyl octanoate), isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate or 2-octyldodecyl myristate or lactate, may be used.

Among the essential oils contained in the composition of the invention, mention may be made of those mentioned in Ullmann's Encyclopedia of Industrial Chemistry ("Flavors and Fragrances", Karl-Georg Fahlbusch et al., Published Online: 15 Jan. 2003, DOI: 10.1002/14356007.a11_141).

According to a preferred variant of the invention, the oil(s) are chosen from $C_6$-$C_{16}$ alkanes, polydecenes, liquid esters of a fatty acid and/or of a fatty alcohol, in particular triglycerides of plant or synthetic origin, and liquid fatty alcohols, or mixtures thereof. Better still, the fatty substance is chosen from liquid esters of a fatty acid and/or of a fatty alcohol, triglycerides of plant or synthetic origin, or mixtures thereof; more preferentially from triglycerides of plant or synthetic origin.

According to another most particularly preferred embodiment of the invention, the oils are chosen from oils of natural origin, more particularly oils of plant origin, preferentially jojoba oil, babassu oil, sunflower oil, olive oil, coconut oil, Brazil nut oil, marula oil, corn oil, argan oil, soybean oil, marrow oil, grapeseed oil, linseed oil, sesame oil, hazelnut oil, apricot oil, macadamia oil, arara oil, coriander oil, castor oil, avocado oil, shea butter oil and also rapeseed oil, borage oil, evening primrose oil, pomegranate oil, mango oil, palm oil and cottonseed oil, or mixtures thereof.

More particularly, the oils of plant origin are chosen from avocado oil, olive oil, coconut oil, argan oil and sunflower oil, or mixtures thereof, better still from coconut oil.

The coconut oil having the INCI name *Cocos nucifera* (coconut) oil will be preferably used.

According to a particular embodiment, the total amount of oil(s) ranges from 0.1% to 20% by weight, more particularly from 0.5% to 15% by weight, preferentially from 1% to 10% by weight, better still from 1.5% to 5% by weight relative to the total weight of the composition.

Preferably, the composition according to the invention comprises one or more oils, more preferentially one or more plant oils.

According to one embodiment, the dye composition according to the invention comprises:
- at least one natural dye chosen from lawsone, henna extracts and/or powders, *Cassia angustifolia* extracts and/or powders, indigo, indigo-producing plant extracts and/or powders, or mixtures thereof;
- at least one triarylmethane synthetic direct dye of formula (IIa1) or (IIa2);
- at least one aromatic compound of formula (I) chosen from benzyl alcohol, phenylethanol and phenoxyethanol, or mixtures thereof, preferably benzyl alcohol;
- at least one oil.

According to a particular embodiment, the composition according to the invention comprises:
- at least one natural dye chosen from lawsone, henna extracts and/or powders, *Cassia angustifolia* extracts and/or powders, indigo, indigo-producing plant extracts and/or powders, or mixtures thereof;
- at least one triarylmethane synthetic direct dye chosen from Basic Violet 1, Basic Violet 2, Basic Violet 3, Basic Violet 4, Basic Violet 14, Basic Blue 1, Basic Blue 7, Basic Blue 26, Basic Green 1, or mixtures thereof, better still from Basic Violet 2, HC Blue 15, or mixtures thereof;
- at least one compound of formula (I), chosen from benzyl alcohol, phenylethanol and phenoxyethanol, or mixtures thereof, preferably benzyl alcohol;
- at least one oil chosen from plant oils, better still from jojoba oil, babassu oil, sunflower oil, olive oil, coconut oil, Brazil nut oil, marula oil, corn oil, argan oil, soybean oil, marrow oil, grapeseed oil, linseed oil, sesame oil, hazelnut oil, apricot oil, macadamia oil, arara oil, coriander oil, castor oil, avocado oil, shea butter oil and also rapeseed oil, borage oil, evening primrose oil, pomegranate oil, mango oil, palm oil and cottonseed oil, or mixtures thereof.

According to this particular embodiment, the total amount of natural dye(s) chosen from lawsone, henna extracts and/or powders, *Cassia angustifolia* extracts and/or powders, indigo, indigo-producing plant extracts and/or powders, or mixtures thereof, preferably ranges from 60% to 90% by weight, relative to the total weight of the composition; the total amount of triarylmethane synthetic direct dye(s) chosen from the dyes of formula ($IIa_1$) or ($IIa_2$), or mixtures thereof, ranges from 0.1% and 13% by weight relative to the total weight of the composition; the total amount of compound(s) of formula (I) chosen from benzyl alcohol, phenylethanol and phenoxyethanol, or mixtures thereof, ranges from 1% to 10% by weight relative to the total weight of the composition; the total amount of oil(s) chosen from plant oils ranges from 1.5% to 5% by weight relative to the total weight of the composition.

According to a preferred embodiment, the composition according to the invention comprises:
- at least one natural dye chosen from lawsone, henna extracts and/or powders, *Cassia angustifolia* extracts and/or powders, indigo, indigo-producing plant extracts and/or powders, or mixtures thereof;
- at least one triarylmethane synthetic direct dye chosen from Basic Violet 2, HC Blue 15, or mixtures thereof;
- at least benzyl alcohol;
- at least coconut oil.

According to this preferred embodiment, the total amount of lawsone, of henna extracts and/or powders, of *Cassia angustifolia* extracts and/or powders, of indigo, of indigo-producing plant extracts and/or powders, or of a mixture thereof, preferably ranges from 60% to 90% by weight, relative to the total weight of the composition; the amount of Basic Violet 2, HC Blue 15, or of mixtures thereof ranges from 0.1% to 13% by weight relative to the total weight of the composition; the amount of benzyl alcohol ranges from 1% to 10% by weight relative to the total weight of the composition, the amount of coconut oil ranges from 1.5% to 5% by weight relative to the total weight of the composition.

(Poly)saccharide(s)

The composition according to the invention may comprise one or more (poly)saccharides.

The saccharides may be chosen from monosaccharides, oligosaccharides and polysaccharides.

In particular, the saccharides or reduced saccharides of the invention are solids, i.e. they are not liquids or syrups.

The term "monosaccharide" means a sugar comprising only one unit, i.e. which does not include any glycosidic covalent bond with another sugar.

Preferentially the "monosaccharides" of the invention are chosen from:
- "aldoses" or polyhydroxyaldehydes, preferably comprising between 4 and 6 carbon atoms, such as erythrose or threose (4 carbon atoms), ribose, arabinose, xylose or lyxose (5 carbon atoms), allose, altrose, glucose, mannose, gulose, idose, galactose and talose (6 carbon atoms);
- "ketoses" or polyhydroxyketones, preferably comprising between 4 and 6 carbon atoms, such as erythrulose (4 carbon atoms), ribulose or xylulose (5 carbon atoms), psicose, fructose, sorbose and tagatose (6 carbon atoms); and
- the reduced forms of the aldoses and ketoses as defined previously are also referred to as "sugar alcohols" or "alditols". They are in particular chosen from erythritol, glucitol or sorbitol, mannitol and xylitol, preferably sorbitol.

The term "sugar alcohol" means "polyols" generally obtained by reduction of the aldose or ketose monosaccharides as defined previously or of oligo- or polysaccharide complexes as defined below, in which the aldehyde or ketone group(s) of the monosaccharide units are reduced, i.e. replaced with a hydroxyl group.

Preferably, the sugars of the invention, and in particular the sugar alcohols according to the invention, are of plant origin.

It is understood that the terms aldoses, ketoses and sugar alcohols also refer to the optical isomers thereof, the anomers thereof and the L (levorotatory) and D (dextrorotatory) forms thereof.

More preferentially, the monosaccharides of the invention include 6 carbon atoms.

The term "oligosaccharide" means a sugar in which the monosaccharides as defined previously are linked via a glycosidic covalent bond, to give simple polymers comprising from 2 to 10 monosaccharide units.

In particular, the oligosaccharides are chosen from disaccharides, such as sucrose, trehalose and raffinose, lactose, cellobiose and maltose; cyclodextrins and reduced forms thereof, such as isomaltulose, trehalulose, isomalt, maltitol, and lactitol.

It is understood that the term "oligosaccharides" also refers to the optical isomers thereof, the anomers thereof and the L (levorotatory) and D (dextrorotatory) forms thereof.

The term "polysaccharides" means oligosaccharides which contain at least 11 monosaccharide units. Preferentially, the polysaccharides of the invention include between 20 and 100 000 monosaccharide units.

The polysaccharides of the invention may be chosen from those derived from the following sugars: glucose; galactose; arabinose; rhamnose; mannose; xylose; fucose; anhydrogalactose; galacturonic acid; glucuronic acid; mannuronic acid; galactose sulfate; anhydrogalactose sulfate.

The polymers bearing sugar units of the invention may be natural or synthetic.

They may be nonionic, anionic, amphoteric or cationic.

According to a particular embodiment, the saccharides of the invention are chosen from native gums such as:
- tree or shrub exudates, for instance: acacia gum (branched polymer of galactose, arabinose, rhamnose and glucuronic); ghatti gum (polymer derived from arabinose, galactose, mannose, xylose and glucuronic acid); karaya gum (polymer derived from galacturonic acid, galactose, rhamnose and glucuronic acid); gum tragacanth (polymer of galacturonic acid, galactose, fucose, xylose and arabinose);
- gums derived from algae, such as: agar (polymer derived from galactose and anhydrogalactose); alginates (polymers of mannuronic acid and glucuronic acid); carrageenans and furcellerans (polymers of galactose sulfate and anhydrogalactose sulfate);
- gums derived from seeds or tubers, such as: guar gum (polymer of mannose and galactose); locust bean gum (polymer of mannose and galactose); fenugreek gum (polymer of mannose and galactose); tamarind gum (polymer of galactose, xylose and glucose); konjac gum (polymer of glucose and mannose);
- plant extracts, such as: cellulose (glucose polymer); and starch (glucose polymer);
- microbial gums, such as: xanthan gums (polymer of glucose, mannose acetate, mannose/pyruvic acid and glucuronic acid); gellan gums (polymer of partially acylated glucose, rhamnose and glucuronic acid); scleroglucan gums (glucose polymer); pullulan gums, curdlar gums, grifolan gums, lentinan gums, schizophyllan gums, spirulinan gums and krestin gums.

For the purposes of the present invention, the term "microbial gums" means substances synthesized by fermentation of sugars by microorganisms.

According to a preferred embodiment, the polysaccharides that are useful according to the invention are chosen from gums, better still from microbial gums. Xanthan gums are preferentially used.

According to one embodiment, the total amount of (poly)saccharide ranges from 0.05% to 10%, preferably from 0.1% to 5% and better still from 0.2% to 2% by weight relative to the total weight of the composition.

According to one embodiment, the dye composition according to the invention comprises:
- at least one natural dye chosen from lawsone, henna extracts and/or powders, Cassia angustifolia extracts and/or powders, indigo, indigo-producing plant extracts and/or powders, or mixtures thereof;
- at least one triarylmethane synthetic direct dye of formula (IIa1) or (IIa2);
- at least one aromatic compound of formula (I) chosen from benzyl alcohol, phenylethanol and phenoxyethanol, or mixtures thereof, preferably benzyl alcohol;
- at least (poly)saccharide.

According to a particular embodiment, the composition according to the invention comprises:
- at least one natural dye chosen from lawsone, henna extracts and/or powders, Cassia angustifolia extracts and/or powders, indigo, indigo-producing plant extracts and/or powders, or mixtures thereof;
- at least one triarylmethane synthetic direct dye chosen from Basic Violet 1, Basic Violet 2, Basic Violet 3, Basic Violet 4, Basic Violet 14, Basic Blue 1, Basic Blue 7, Basic Blue 26, Basic Green 1, or mixtures thereof, better still from Basic Violet 2, HC Blue 15, or mixtures thereof;
- at least one compound of formula (I), chosen from benzyl alcohol, phenylethanol and phenoxyethanol, or mixtures thereof, preferably benzyl alcohol;
- at least one (poly)saccharide chosen from gums, better still from microbial gums, or mixtures thereof.

According to this particular embodiment, the total amount of natural dye(s) chosen from lawsone, henna extracts and/or powders, Cassia angustifolia extracts and/or powders, indigo, indigo-producing plant extracts and/or powders, or mixtures thereof, preferably ranges from 60% to 90% by weight, relative to the total weight of the composition; the total amount of triarylmethane synthetic direct dye(s) chosen from the dyes of formula (IIa$_1$) or (IIa$_2$), or mixtures thereof, ranges from 0.1% to 13% by weight relative to the total weight of the composition; the total amount of compound(s) of formula (I) chosen from benzyl alcohol, phenylethanol and phenoxyethanol, or mixtures thereof, ranges from 1% to 10% by weight relative to the total weight of the composition; the total amount of (poly)saccharide(s) chosen from gum(s) ranges from 0.2% to 2% by weight relative to the total weight of the composition.

According to a preferred embodiment, the composition according to the invention comprises:
- at least one natural dye chosen from lawsone, henna extracts and/or powders, Cassia angustifolia extracts and/or powders, indigo, indigo-producing plant extracts and/or powders, or mixtures thereof;
- at least one triarylmethane synthetic direct dye chosen from Basic Violet 2, HC Blue 15, or mixtures thereof;
- at least benzyl alcohol;
- at least one (poly)saccharide chosen from xanthan gums.

According to this preferred embodiment, the total amount of lawsone, of henna extracts and/or powders, of Cassia angustifolia extracts and/or powders, of indigo, of indigo-producing plant extracts and/or powders, or of a mixture thereof, preferably ranges from 60% to 90% by weight, relative to the total weight of the composition; the total amount of Basic Violet 2, HC Blue 15, or of mixtures thereof, ranges from 0.1% and 13% by weight relative to the total weight of the composition; the amount of benzyl alcohol ranges between 1% to 10% by weight relative to the total weight of the composition, the total amount of xanthan gums, or mixtures thereof, ranges from 0.2% to 2% by weight relative to the total weight of the composition.

According to one embodiment, the dye composition according to the invention comprises:
- at least one natural dye chosen from lawsone, henna extracts and/or powders, Cassia angustifolia extracts and/or powders, indigo, indigo-producing plant extracts and/or powders, or mixtures thereof;
- at least one triarylmethane synthetic direct dye of formula (IIa1) or (IIa2);
- at least one aromatic compound of formula (I) chosen from benzyl alcohol, phenylethanol and phenoxyethanol, preferably benzyl alcohol;
- at least one additional synthetic direct dye, and/or at least one oil, and/or at least one (poly)saccharide.

According to a particular embodiment, the composition according to the invention comprises:
- at least one natural dye chosen from lawsone, henna extracts and/or powders, Cassia angustifolia extracts and/or powders, indigo, indigo-producing plant extracts and/or powders, or mixtures thereof;
- at least one triarylmethane synthetic direct dye chosen from Basic Violet 1, Basic Violet 2, Basic Violet 3, Basic Violet 4, Basic Violet 14, Basic Blue 1, Basic Blue 7, Basic Blue 26, Basic Green 1, or mixtures thereof, better still from Basic Violet 2, HC Blue 15, or mixtures thereof;
- at least one compound of formula (I), chosen from benzyl alcohol, phenylethanol and phenoxyethanol, or mixtures thereof, preferably benzyl alcohol;
- at least one additional synthetic direct dye chosen from hydrazono, azo, nitro(hetero)aryl and anthraquinone dyes, or mixtures thereof, and/or at least one oil chosen from plant oils, better still from jojoba oil, babassu oil, sunflower oil, olive oil, coconut oil, Brazil nut oil, marula oil, corn oil, argan oil, soybean oil, marrow oil, grapeseed oil, linseed oil, sesame oil, hazelnut oil, apricot oil, macadamia oil, arara oil, coriander oil, castor oil, avocado oil, shea butter oil and also rapeseed oil, borage oil, evening primrose oil, pomegranate oil, mango oil, palm oil, cottonseed oil, or mixtures thereof, and/or at least one (poly)saccharide chosen from gums, better still from microbial gums, or mixtures thereof.

According to a preferred embodiment, the composition according to the invention comprises:
- at least one natural dye chosen from lawsone, henna extracts and/or powders, Cassia angustifolia extracts and/or powders, indigo, indigo-producing plant extracts and/or powders, or mixtures thereof;

at least one triarylmethane synthetic direct dye chosen from Basic Violet 2, HC Blue 15, or mixtures thereof;
at least benzyl alcohol;
at least one additional synthetic direct dye chosen from Basic Yellow 87, Basic Red 51, Basic Orange 31, HC Blue 2 and HC Blue 16, or mixtures thereof, and/or at least coconut oil, and/or at least one (poly)saccharide chosen from xanthan gums.

Solvent(s)

The composition according to the invention may comprise at least one aliphatic organic solvent.

According to one embodiment, the aliphatic organic solvent(s) are chosen from $C_2$-$C_6$ hydroxylated aliphatic solvents. The term "aliphatic" refers to a compound not containing any aromatic nuclei. The solvents of this type may be monoalcohols or polyalcohols that are liquid at room temperature (25° C.) and at atmospheric pressure (105 Pa). Preferably, these solvents are nonetherified solvents. According to a particular embodiment, these solvents are chosen from ethanol, glycerol, propylene glycol, dipropylene glycol and hexylene glycol. Preferably, the hydroxylated $C_2$-$C_6$ aliphatic solvent is ethanol and/or hexylene glycol, preferably ethanol.

According to one embodiment, the amount of hydroxylated aliphatic solvent ranges from 0.05% to 10%, preferably from 1% to 8%, better still from 2% to 5%, by weight relative to the total weight of the composition.

Adjuvant(s)

The compositions of the dyeing process in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers other than the polysaccharides as described previously, or mixtures thereof, mineral or organic thickeners other than the polysaccharides as described previously, and in particular anionic, cationic, nonionic and amphoteric polymeric associative thickeners, antioxidants, penetrants, sequestrants, fragrances, buffers, dispersants, conditioning agents, for instance volatile or nonvolatile, modified or unmodified silicones, film-forming agents, ceramides, preserving agents and opacifiers.

The above adjuvants are generally present in an amount for each of them of between 0.01% and 40% by weight relative to the weight of the composition, and preferably between 0.1% and 20% by weight relative to the weight of the composition.

Needless to say, a person skilled in the art will take care to select this or these additional compound(s) such that the advantageous properties intrinsically associated with the composition(s) that are useful in the dyeing process in accordance with the invention are not, or are not substantially, adversely affected by the envisioned addition(s).

The composition according to the invention may be anhydrous or aqueous.

In one embodiment, the composition according to the invention is anhydrous. For the purposes of the present invention, the term "anhydrous" means that the composition comprises less than 5% by weight of water and preferably less than 2% by weight of water; better still, the composition is free of water. In particular, the composition is free of added water, the water optionally present being provided by the raw materials used.

In another embodiment, the composition according to the invention is aqueous. In this embodiment, the composition may result from the mixture of a composition (A) according to the invention, which is preferably anhydrous, with at least one composition (B) which is preferably aqueous.

The cosmetic composition(s) used according to the process according to the invention may be in various presentation forms, such as a powder, a lotion, a mousse, a cream or a gel, or in any other form that is suitable for dyeing keratin fibers. They may also be packaged in a propellant-free pump-action bottle or under pressure in an aerosol container in the presence of a propellant and form a foam.

Dyeing Process

The process for dyeing of human keratin fibers, notably the hair, according to the invention consists in applying to the fibers a composition comprising at least one natural dye;
at least one triarylmethane synthetic direct dye; and
at least one aromatic compound of formula (I) to the dry or wet human keratin fibers, such as the hair.

The composition applied may be obtained by extemporaneous mixing at the time of use of a composition (A) comprising at least one natural dye;
at least one triarylmethane synthetic direct dye; and
at least one aromatic compound of formula (I), and at least one composition (B) which is preferably aqueous.

In a particular embodiment, composition (B) is water.

Preferably, composition (B) is used at a temperature of between 10° C. and 100° C., better still between 40° C. and 100° C.

The mixing ratio between composition (A) and composition (B) may range from 0.01 to 10, preferably from 0.1 to 5, preferentially from 0.2 to 1, and better still from 0.25 to 0.5.

According to this embodiment, the mixing of compositions (A) and (B) is preferably performed less than 30 min before application, preferentially less than 15 min before application, better still less than 10 min before application, or even less than 5 min before application.

According to a particular embodiment, the applied composition contains at least one additional direct dye, at least one oil and/or one or more (poly)saccharides.

The composition is then left in place for a time usually ranging from 1 minute to 2 hours, preferably from 5 minutes to 1 hour 30 minutes and better still from 10 minutes to 1 hour.

Advantageously, after application of the dye composition, the hair may be subjected to a heat treatment. In practice, this operation may be performed using a hairstyling hood, a hairdryer, an infrared ray emitter or other standard heating appliances.

The temperature during the process is conventionally between room temperature (between 15 and 25° C.) and 80° C. and preferably between room temperature and 60° C.

After the treatment, the human keratin fibers are optionally rinsed with water, optionally washed with a shampoo and then rinsed with water, before being dried (mechanically with a towel, absorbent paper or heat) or left to dry.

According to a second embodiment, the process as described above is preceded (i) by a step of applying a dye composition as described previously or a dye composition comprising a natural dye and free from synthetic direct dyes; (ii) by a rinsing step.

The examples that follow serve to illustrate the invention without, however, being limiting in nature.

EXAMPLES

Comparative Tests 1

Compositions A and B were prepared. The proportions of the ingredients are indicated as grams of active material per 100 grams of composition.

Composition According to the Invention and Comparative Composition:

TABLE 1

| Ingredients | A (inv) | B (comp) |
| --- | --- | --- |
| Cassia angustifolia leaf powder, sold by the company Kankor | 84.9 | 84.9 |
| Basic Violet 2 | 4 | |
| HC Blue 2 | | 4 |
| Coconut oil | 2.5 | 2.5 |
| Xanthan gum | 0.6 | 0.6 |
| Benzyl alcohol | 8 | 8 |

Composition B comprises a blue dye which is not a triarylmethane synthetic direct dye but a nitrobenzene dye.

At the time of use, each of the dye compositions A and B is mixed with three times its own weight of water at 100° C.

Each of the mixtures is then applied to locks of natural hair containing 90% white hairs, at a rate of 10 g of mixture per 1 g of hair.

After leaving it on plates thermostatically maintained at 33° C. for 30 minutes, the hair is rinsed and dried.

Evaluation of the Coloring

The coloring of the hair is evaluated in the L*a*b* system, using a Minolta CM 3600D spectrocolorimeter (illuminant D65, angle 10°, specular component included).

In this system, L* represents the lightness. The smaller the value of L*, the darker and more powerful the coloring obtained. The chromaticity is measured by the values a* and b*, a* representing the red/green axis and b* the yellow/blue axis.

The color buildup is represented by the color difference A E between the undyed lock and the dyed lock: the greater the value of A E, the greater the color buildup. This value is calculated from the following equation (i):

$$\Delta E = \sqrt{(L^* - L_o^*)^2 + (a^* - a_o^*)^2 + (b^* - b_o^*)^2} \quad (i)$$

In the equation (i), L*, a* and b* represent the values measured on locks of undyed hair and $L_0^*$, $a_0^*$ and $b_0^*$ represent the values measured on locks of dyed hair.

Dyeing Results

The colorimetric values and the color buildup A E are listed in the table below:

Better color buildup was obtained on the locks of hair treated using the composition according to the invention, which is confirmed by the colorimetric measurements below.

TABLE 2

| Composition | a* | b* | ΔE |
| --- | --- | --- | --- |
| before dyeing | 1.26 | 12.76 | — |
| Composition A (inv) | 38.37 | −8.38 | 51.05 |
| Composition B | 7.40 | −11.23 | 36.19 |

The above results show that better color buildup and more powerful coloring were obtained using composition A according to the invention, relative to comparative composition B not comprising a triarylmethane synthetic direct dye.

Comparative Tests 2

TABLE 3

| Ingredients | C (inv) | D (comp) | E (comp) |
| --- | --- | --- | --- |
| Cassia angustifolia leaf powder, sold by the company Kankor | 88.2 | 88.2 | 88.2 |
| HC Blue 15 | 0.3 | 0.3 | 0.3 |
| Basic Red 51 | 1 | 1 | 1 |
| Coconut oil | 2.5 | 2.5 | 2.5 |
| Benzyl alcohol | 8 | | |
| Ethanol | | 8 | |
| Propylene glycol | | | 8 |

Compositions D and E do not contain any aromatic compound of formula (I).

At the time of use, each of the dye compositions C, D and E is mixed with three times its weight of water at 100° C.

Each of the mixtures is then applied to locks of natural hair containing 90% white hairs, at a rate of 10 g of mixture per 1 g of hair.

After leaving it on plates thermostatically maintained at 33° C. for 30 minutes, the hair is rinsed and dried.

The dyeing performance is evaluated in the same manner as previously.

The results obtained are as follows:

TABLE 4

| Composition | a* | b* | ΔE |
| --- | --- | --- | --- |
| before dyeing | 2.18 | 16.48 | — |
| Composition C (inv) | 20.04 | −5.76 | 40.13 |
| Composition D | 19.20 | −4.47 | 35.17 |
| Composition E | 21.10 | −5.49 | 36.27 |

Composition C according to the invention results in better color buildup and in more powerful coloring, relative to comparative compositions D and E.

The invention claimed is:

1. A composition for dyeing human keratin fibers, comprising:
    at least one natural dye;
    at least one triarylmethane synthetic direct dye; and
    at least one aromatic compound of formula (I), $$(X)n\text{—}\bigcirc\text{—}Y \quad (I)$$

wherein:
    Y represents a $C_1$-$C_4$ hydroxyalkyl group or a $C_1$-$C_4$ hydroxyalkyloxy radical,
    n denotes an integer ranging from 0 to 5, and
    X, which may be identical or different, represents a $C_1$-$C_4$ alkyl radical or a halogen.

2. The composition of claim 1, wherein the at least one natural dye is chosen from lawsone, henna extracts, henna powders, Cassia angustifolia extracts, Cassia angustifolia powders, indigo, indigo-producing plant extracts, indigo-producing plant powders, or mixtures thereof.

3. The composition of claim 1, wherein the total amount of the at least one natural dye ranges from 40% to 98% by weight, relative to the total weight of the composition.

4. The composition of claim 1, wherein the at least one triarylmethane synthetic direct dye is chosen from the cationic dyes of formulae (IIa1) and (IIa2) below, addition salts thereof with an organic or mineral acid or base, geometrical isomers thereof, optical isomers thereof, tautomers thereof, mesomeric forms thereof, solvates thereof, or mixtures thereof:

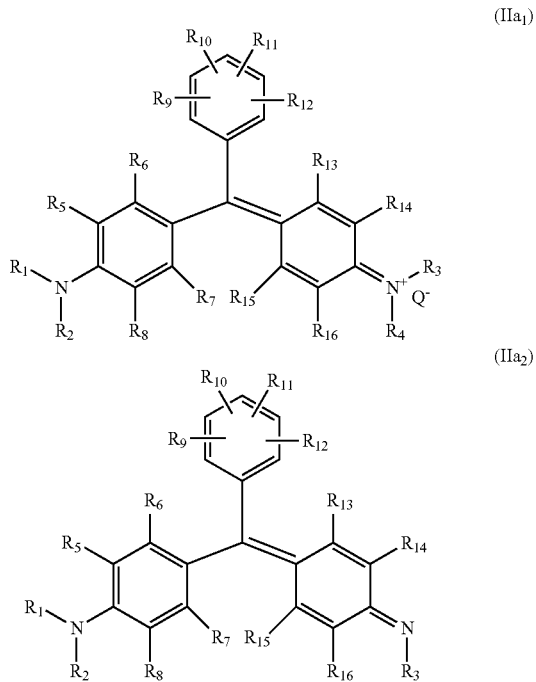

wherein:
R1, R2, R3, and R4, which may be identical or different, represent a hydrogen atom or a group chosen from: $(C_1-C_6)$alkyl which is optionally substituted; aryl, aryl$(C_1-C_4)$alkyl, heteroaryl, heteroaryl$(C_1-C_4)$ alkyl, or alternatively two groups R1 and R2, and/or R3 and R4, borne by the same nitrogen atom form, together with the nitrogen atom which bears them, an optionally substituted heterocycloalkyl group;
R5, R6, R7, R8, R9, R10, R11, R12, R13, R14, R15, and R16, which may be identical or different, represent a hydrogen atom, halogen atom, or a group chosen from:
i) hydroxyl;
ii) thiol;
iii) amino;
iv) (di)$(C_1-C_4)$(alkyl)amino;
v) (di)arylamino;
vi) nitro;
vii) acylamino (—NR—C(O)R') in which the radical R is chosen from a hydrogen atom or a $C_1$-$C_4$ alkyl radical optionally bearing at least one hydroxyl group, and the radical R' is a $C_1$-$C_2$ alkyl radical;
viii) carbamoyl ((R)$_2$N—C(O)—), wherein the radicals R, which may be identical or not, represent a hydrogen atom or a $C_1$-$C_4$ alkyl radical optionally bearing at least one hydroxyl group;
ix) carboxylic acid (—O—C(O)R') wherein the radical R' is a hydrogen atom or $C_1$-$C_4$ alkyl optionally bearing at least one hydroxyl group or ester (—C(O)OR'), wherein the radical R' is a $C_1$-$C_2$ alkyl radical;
x) alkyl which is optionally substituted;
xi) alkylsulfonylamino (R'SO$_2$—NR—), wherein the radical R represents a hydrogen atom or a $C_1$-$C_4$ alkyl radical optionally bearing at least one hydroxyl group, and the radical R' represents a $C_1$-$C_4$ alkyl radical or a phenyl radical;
xii) aminosulfonyl ((R)$_2$N—SO$_2$—), wherein the radicals R, which may be identical or not, represent a hydrogen atom or a $C_1$-$C_4$ alkyl radical optionally bearing at least one hydroxyl group;
xiii) $(C_1-C_4)$alkoxy; and
xiv) $(C_1-C_4)$alkylthio; or
alternatively, two radicals borne by two contiguous carbon atoms R5 and R6, R7 and R8, R9 and R10, R11 and R12, R13 and R14, and/or R15 and R16 form, together with the carbon atoms which bear them, a fused 6-membered aryl or heteroaryl ring, wherein said ring may be optionally substituted; and
Q⁻ represents an anionic counterion to achieve electrical neutrality.

5. The composition of claim 4, wherein in formulae (IIa1) and (IIa2), R1, R2, R3, and R4, which may be identical or different, represent a hydrogen atom or a $(C_1-C_4)$alkyl group.

6. The composition of claim 4, wherein Q⁻ represents an halide or phosphate.

7. The composition of claim 1, wherein the at least one triarylmethane synthetic direct dye is chosen from Basic Violet 1, Basic Violet 2, Basic Violet 3, Basic Violet 4, Basic Violet 14, Basic Blue 1, Basic Blue 7, Basic Blue 26, Basic green 1, HC Blue 15, or mixtures thereof.

8. The composition of claim 1, wherein the total amount of the at least one triarylmethane synthetic direct dye ranges from 0.01% to 20% by weight, relative to the total weight of the composition.

9. The composition of claim 1, wherein the at least one aromatic compound of formula (I) is chosen from benzyl alcohol, phenylethanol, phenoxyethanol, or mixtures thereof.

10. The composition of claim 1, wherein the at least one aromatic compound of formula (I) comprises benzyl alcohol.

11. The composition of claim 1, wherein the total amount of the at least one aromatic compound of formula (I) ranges from 0.1% to 20% by weight, relative to the weight of the composition.

12. The composition of claim 1, further comprising at least one additional synthetic direct dye.

13. The composition of claim 12, wherein the at least one additional synthetic direct dye is chosen from azo dyes, hydrazono dyes, nitro(hetero)aryl dyes, or mixtures thereof.

14. The composition of claim 12, wherein the total amount of the at least one additional synthetic direct dye ranges from 0.01% to 15% by weight, relative to the total weight of the composition.

15. The composition of claim 1, further comprising at least one oil.

16. The composition of claim 15, wherein the total amount of the at least one oil ranges from 0.1% to 20% by weight, relative to the total weight of the composition.

17. The composition of claim 1, further comprising at least one (poly)saccharide.

18. The composition of claim 17, wherein the total amount of the at least one (poly)saccharide ranges from 0.05% to 10% by weight, relative to the total weight of the composition.

19. A process for dyeing keratin fibers comprising:
applying to the keratin fibers a composition comprising:
  at least one natural dye;
  at least one triarylmethane synthetic direct dye; and
  at least one aromatic compound of formula (I),

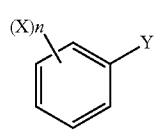

(I)

wherein:
  Y represents a $C_1$-$C_4$ hydroxyalkyl group or a $C_1$-$C_4$ hydroxyalkyloxy radical,
  n denotes an integer ranging from 0 to 5, and
  X, which may be identical or different, represents a $C_1$-$C_4$ alkyl radical or a halogen.

20. A process for dyeing keratin fibers, comprising:
applying to the keratin fibers a composition resulting from extemporaneous mixing at the time of use a composition (A) and an aqueous composition (B), at a mixing ratio of the composition (A) to the aqueous composition (B) ranging from 0.01 to 10, wherein composition (A) comprises:
  at least one natural dye;
  at least one triarylmethane synthetic direct dye; and
  at least one aromatic compound of formula (I),

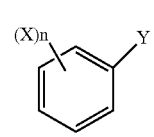

(I)

wherein:
  Y represents a $C_1$-$C_4$ hydroxyalkyl group or a $C_1$-$C_4$ hydroxyalkyloxy radical,
  n denotes an integer ranging from 0 to 5, and
  X, which may be identical or different, represents a $C_1$-$C_4$ alkyl radical or a halogen.

* * * * *